United States Patent [19]
Ditkoff et al.

[11] Patent Number: 6,066,449
[45] Date of Patent: May 23, 2000

[54] METHOD OF DETECTING METASTATIC THYROID CANCER

[75] Inventors: Beth Ann Ditkoff, New York; John A. Chabot, Rye, both of N.Y.; Carl R. Feind, Alpine, N.J.; Paul LoGerfo, Grandview, N.Y.

[73] Assignee: The Trustees of Columbia University in the City of New York, New York, N.Y.

[21] Appl. No.: 08/840,551

[22] Filed: Apr. 15, 1997

[51] Int. Cl.⁷ .............................. C12Q 1/68; C12P 19/34; C07H 21/04; C07H 21/02
[52] U.S. Cl. ........................ 435/6; 435/91.2; 536/24.33
[58] Field of Search ................... 435/6, 91.2; 536/24.33; 935/77, 78

[56] References Cited

PUBLICATIONS

Ringel et al., J. Clin. Endocrinol. Metab. 83(12):4189–90, Dec. 1998.
Burchill, S.A., et al. (1994) "Neuroblastoma cell detection by reverse transcriptase–polymerase chain reaction (RT–PCR) for tyrosine hydroxylase mRNA." *Int. J. Cancer* 57: 671–675.
Ditkoff, B.A., et al. (1996) "Detection of circulating thyroid cells in peripheral blood." *Surgery* 120: 959–965.
Goldblatt, S.A. and Nadel, E.M. (1965) "Cancer cell in the circulating blood: a critical review II." *Acta Cytologica* 9: 6–20.
Jiang, H., et al. (1994) "Induction of differentiation in human promyelocytic HL–60 leukemia cells activates p21, WAF1/CIP1, expression in the absence of p53." *Oncogene* 9: 3397–3406.
Johnson, P.W.M., et al. (1995) "The molecular detection of circulating tumor cells." *British Journal of Cancer* 72: 268–276.
Katz, A.E., et al. (1994) "Molecular staging of prostate cancer with the use of an enhanced reverse transcriptase–PCR assay." *Urology* 43: 765–775.
Lewis, R. (1997) "RT–PCR may ease testing of patients with throid cancer." *Genetic Engineering News* vol. 17, No. 6, p. 1.
Lo Gerfo, P., et al. (1970) "Thyroglobulin in benign and malignant thyroid disease." *JAMA* 241: 923–925.
Mattano, L.A., et al. (1992) "Sensitive detection of rare circulating neuroblastoma cells by the reverse transcriptase–polymerase chain reaction." *Cancer Research* 52: 4701–4705.
Seiden, M.V., et al. (1994) "Detection of circulating tumor cells in men wtih localized prostate cancer." *Journal of Clinical Oncology* 12: 2634–2639.

*Primary Examiner*—Stephanie Zitomer
*Attorney, Agent, or Firm*—John P. White; Cooper & Dunham LLP

[57] ABSTRACT

This invention provides a method of detecting metastatic thyroid cancer in a subject which comprises detecting circulating thyroid cells in a bodily fluid sample of the subject by obtaining an appropriate nucleic acid sample from the bodily fluid sample of the subject; and determining whether the nucleic acid sample contains a marker sequence. Specifically, this invention provides wherein the marker sequence is mRNA corresponding to the reverse transcript of DNA encoding thyroglobulin. Also, this invention provides wherein the marker sequence is mRNA corresponding to the reverse transcript of DNA encodes thyroid peroxidase. This invention further provides a test kit for performing the above-described method.

14 Claims, 10 Drawing Sheets

P1  5'-GCCTCCATCTGCTGGGTGTC-3'

P2  5'-CTCCCTCCGCAGAACACTGGGGT-3'

THYROGLOBULIN 5' REGION GENE MAP

FIG. 4

```
                                                G
GCC TCC ATC TGC TGG GTG TCG GCC AAT ATC TTC GAG TAC CAG GTT GAT
GCC CAG CCC CTT CGT CCC TGT GAG CTG CAG AGG GAA ACG GCC TTT
CTG AAG CAA GCA GAC TAC GTG CCC CAG TGT GCA GAG GAT GGC AGC
TTC CAG ACT GTC CAG TGC CAG AAC GAC GGC CGC TCC TGC TGG TGT
GTG GGT GCC AAC GGC AGT GAA GTG CTG GGC AGC AGG CAG CCA GGA
CGG CCT GTG GCT TGT GTG TCA TTT TGT CAG CTA CAG AAA CAG CAG ATC
TTA CTG AGT GGC TAC ATT AAC AGC ACA GAC TAC CTC TAC CTC CCT CAG
TGT CAG GAT TCA GGG GAC TAC GCG CCT GTT CAG TGT GAT GTG CAG CAT
GTC CCA GTG CTG GTG TGT GGA CGC AGA GGG GAT GGA GGT GTA TGG
GAC CCG CCA GCT GGG GAG GCC AAA GCG ATG TCC AAG GAG CTG TGA
AAT AAG AAA TCG TCG TCT TCT CCA CGG GGT GGG AGA TAA GTC ACC ACC
CCA GTG TTC TGC GGA GGG AG
``` with TSH stimulation

B: Before operation
A: After operation

B: Before operation
A: After operation

FIG. 7A

5' AGG AGT CTC GTG TCT CTA G 3'

FIG. 7B

5' GAC TGA AGC CGT CCT CAT A 3'

FIG. 7C

5'-end primer AGGAGTCTCGTGTCTCTA

GTCTTGGAGG AAAGCAAGCG CCTGGTGGAC ACCGCCATGT ACGCCACGAT
GCAGAGAAAC CTCAAGAAAA GAGGAATCCT TTCTCCAGCT CAGCTTCTGT
CTTTTTCCAA ACTTCCTGAG CCAACAAGCG GAGTGATTGC CCGAGCAGCA
GAGATAATGG AAACATCAA

FIG. 7D

3'-end primer GACTGAAGCCGTCCTCATA

GACTGGAGGG AGCCATCCGTG CCAGGGCCGT GTTGGAGGCG CCCCATCTGG
GGTGGTCTCT GTTGTTGCAA GCTCCTGTGA TGGGCCTGTA TTTGTTCGCC
AGGCAAGTGT TTGGGCATTT TGGGGGCAGC ATGTAAGGGA GACATCCAGA
CATGTTTGCA ATGATGCTCA GCAGATCTTC TGATAAAGCA TCCGTTGGAT
GCTGTGATTG TTGAGTTTTC AGGTTGACTT TTCTTTTCAT CGCTTGTATT
GATGTTTCCA TTATCTCTGC TGCTCGGGGA ATCACTCCGC TTGTTGGCTC
AGGAAGTTTG GAAAAA

Throughout this application, various publications are referenced by author and date. Full citations for these publications may be found listed alphabetically at the end of the specification immediately before the claims. The disclosures of these publications in their entireties are hereby incorporated by reference into this application in order to more fully describe the state of the art as known to those skilled therein.

BACKGROUND OF THE INVENTION

Differentiated thyroid cancer is the most common endocrine malignancy (Cady, B. and Rossi, R. L. , 1991). In the United States, there are approximately 14,000 new patients and 1,100 deaths per year (Shah, J. P. and Lydiatt, W., 1995). Follicular cancers generally metastasize via hematogenous dissemination, whereas papillary cancers spread through lymphatic involvement. Patients with distant metastatic disease have the worst prognosis (Braverman, L. E., et al., 1991).

Current techniques to detect metastases include nuclear scans (such as $^{131}$I scanning) as well as measurement of serum thyroglobulin. Detectable serum thyroglobulin levels are found in normal patients as well as some types of benign thyroid disease (LoGerfo, P., et al., 1979).

Thyroglobulin is a large glycoprotein (molecular weight of 660,000) secreted exclusively by the thyroid follicular cell and is often elevated in patients with differentiated thyroid malignancies.

Thyroid peroxidase is a membrane-bound glycosylated, hemoprotein enzyme that plays a key role in thyroid hormone biosynthesis by catalyzing both the iodination of tyrosyl residues and the coupling of iodotyrosyl residues in thyroglobulin. Until 1985, this was considered to be its only role in the thyroid; however, thyroid peroxidase is closely related to, if not identified with, the thyroid microsomal antigen associated with the antithyroid microsomal autoantibodies found in the serum of many patients with autoimmune thyroid disease.

The detection of small numbers of circulating thyroid cells has previously been impossible due to insensitive techniques. With polymerase chain reaction (PCR), however, it is now possible to utilize a tissue-specific gene expression approach to detect circulating thyrocytes. This technique has also been utilized with other solid tumors such as prostate and neuroblastoma (Moreno, J. G., et al., 1992; Katz, A. E., et al., 1994; Seiden, M. V., et al., 1994; Mattano, L. A., et al., 1992; Burchill, S. A., et al., 1994; Johnson, P. W. M., et al., 1995). Thyroglobulin and thyroid peroxidase are two examples of proteins that are expressed specifically in thyrocytes. Since it is believed that patients with thyroid cancer and metastatic thyroid cancer will have circulating thyroid cells in the peripheral bloodstream, whereas those patients without thyroid cancer will not, one could use PCR to amplify the mRNA transcripts of these proteins in order to detect circulating thyroctyes. The detection of circulating thyrocytes may have important significance in the diagnosis and prognosis of thyroid cancer.

SUMMARY OF THE INVENTION

This invention provides a method of detecting metastatic thyroid cancer in a subject which comprises detecting circulating thyroid cells in a bodily fluid sample of the subject by obtaining an appropriate nucleic acid sample from the bodily fluid sample of the subject; and determining whether the nucleic acid sample contains a marker sequence.

In a specific embodiment of the above-described method, the marker sequence is mRNA corresponding to the reverse transcript of DNA encoding thyroglobulin. One skilled in the art may determine whether the nucleic acid sample contains mRNA corresponding to the reverse transcript of DNA encoding thyroglobulin by amplifying the nucleic acid present in the nucleic acid sample, and detecting the presence of thyroglobulin in the resulting amplified nucleic acid. One could amplify the nucleic acid using a pair of appropriate primers.

In another embodiment of the above-described method, the marker sequence is mRNA corresponding to the reverse transcript of DNA encodes thyroid peroxidase.

This invention also provides when bodily fluid sample of the above-described method comprises blood.

This invention also provides when the subject of the above-described method is human.

This invention also provides a test kit for performing the above-described method. Specifically, this invention also provides the above-described test kit, wherein the kit comprises specific primers specific for amplification of nucleic acid encoding thyroglobulin or thyroid peroxidase.

1A. Sequences of the primers used to detect thyroglobulin. Primer P1 (Seq. ID No. 1) and primer P2 (Seq. ID No. 2).

Figure 2A:
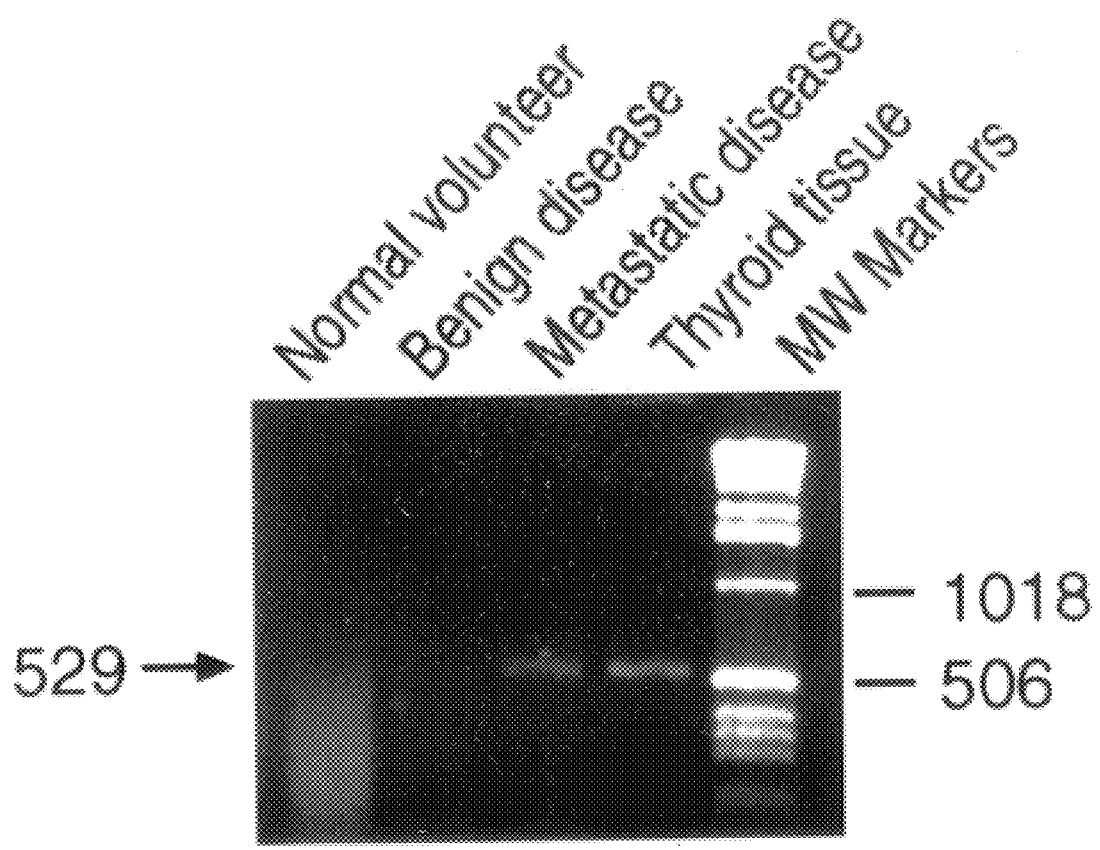

1B. Schematic representation of a portion of the thyroglobulin gene showing the relative position of the specific PCR primers. Primers P1 and P2 bind sequences such that RT-PCR amplification yields an approximately 529 base-pair transcript (FIG. 2A). Primer P1 to Primer P2 genomic DNA length measures approximately 6.5 kbp.

Figure 2B:
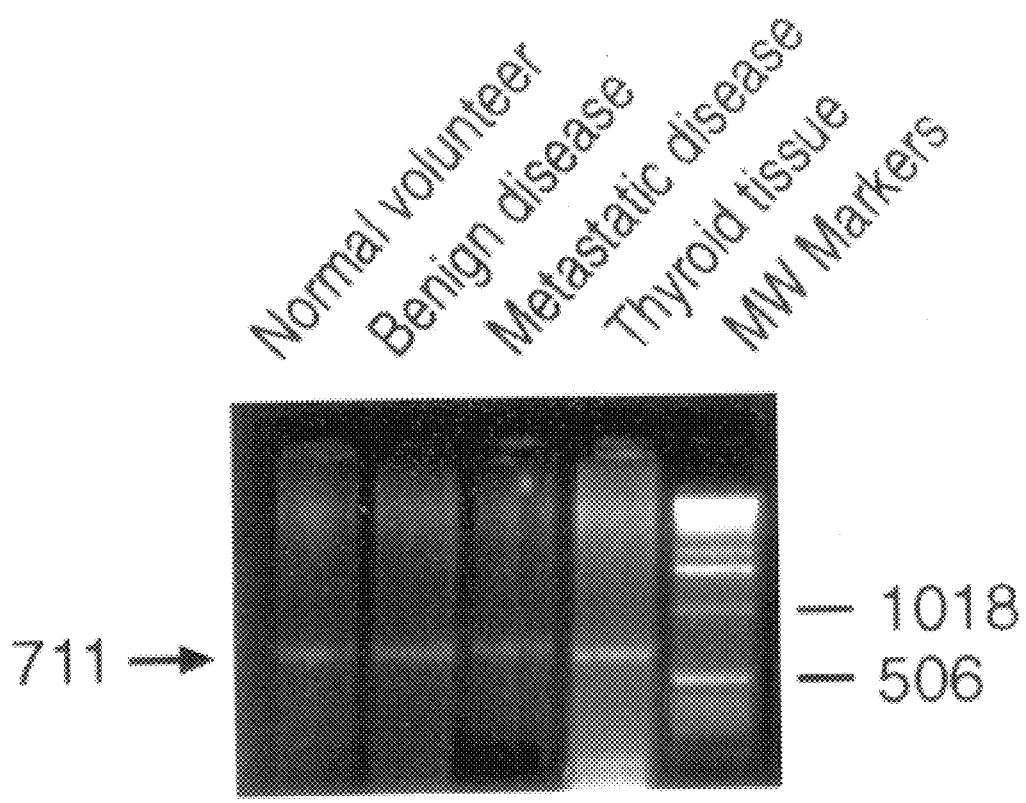

FIGS. 2A and 2B

2A. Thyroglobulin reverse transcriptase polymerase chain reaction (RT-PCR). RT-PCR assay identifies expression of thyroglobulin (approximately 529 bp band) in the peripheral blood of patients with metastatic thyroid cancer and in a specimen of human thyroid tissue. Inability to detect thyroglobulin synthesizing cells in peripheral blood of patients with benign thyroid disease or healthy control volunteers is demonstrated by the absence of the 529 bp band.

2B. Human glyceraldehyde 3-phosphate dehydrogenase (GAPDH) reverse transcriptase polymerase chain reaction (RT-PCR). GAPDH primers were utilized in a parallel reaction and these primers amplified the appropriate 711 bp fragment from all specimens.

Figure 3:
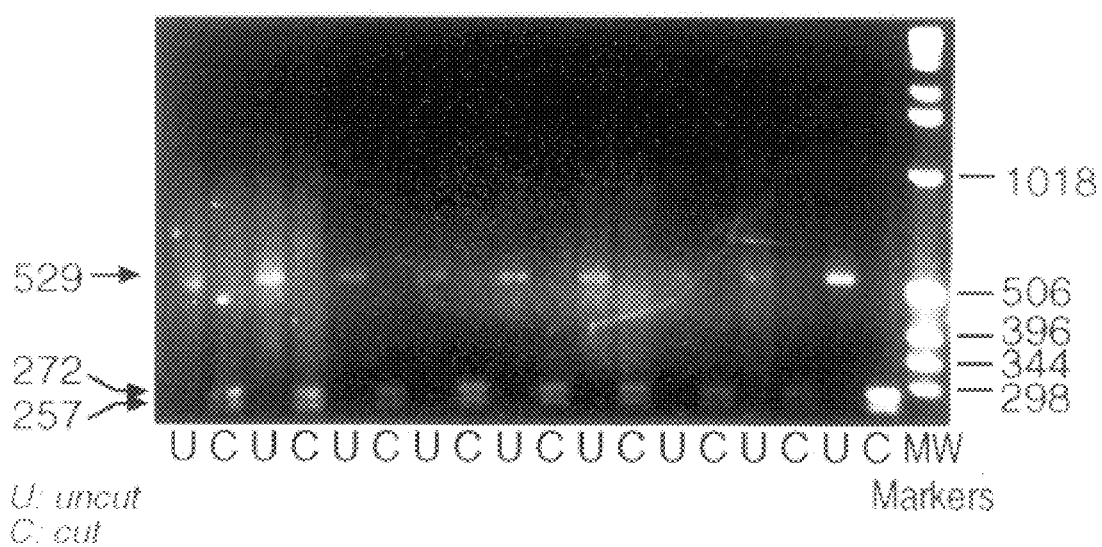

FIG. 3 Verification of amplified fragment by restriction enzyme mapping. Amplified thyroglobulin fragments were isolated from agarose gels by electroelution and DNA was digested with restriction enzymes and analyzed on an agarose gel. The uncut sample (U) measures approximately 529 bp, while the cut samples (C) are approximately 257 bp and 272 bp, respectively. Paired samples (both uncut and cut) are shown for a representative nine patients.

FIG. 4 Nucleotide sequence of thyroglobulin RT-PCR fragment SEQ ID No. 3.

Figure 5A:
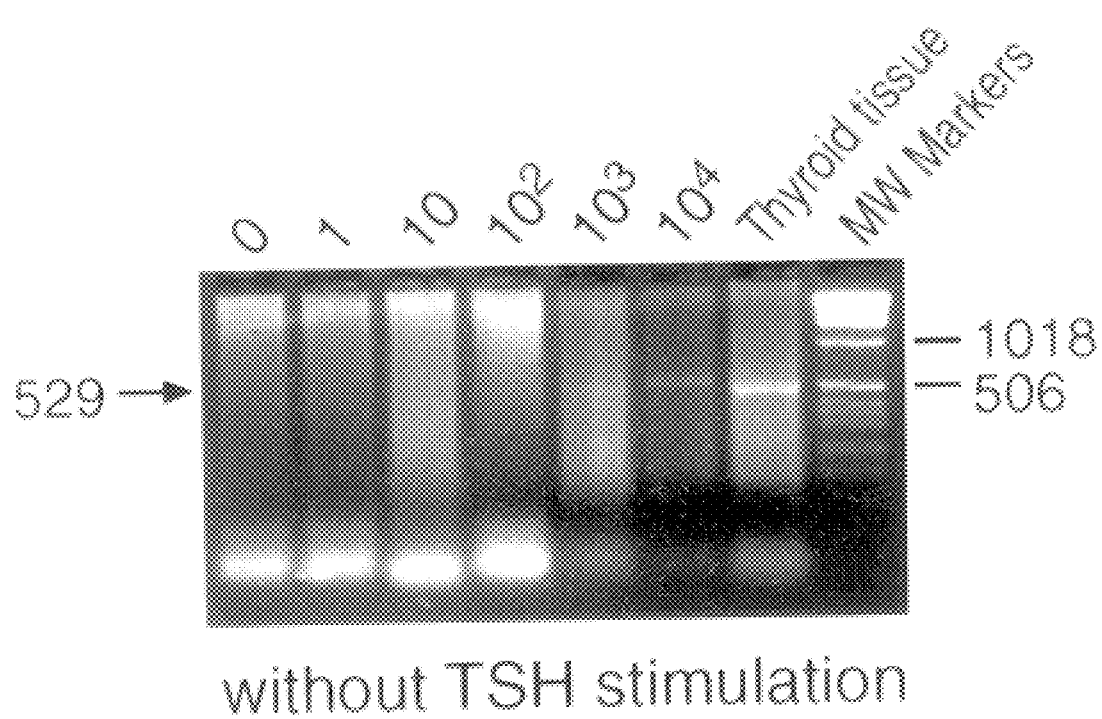
Figure 5B:
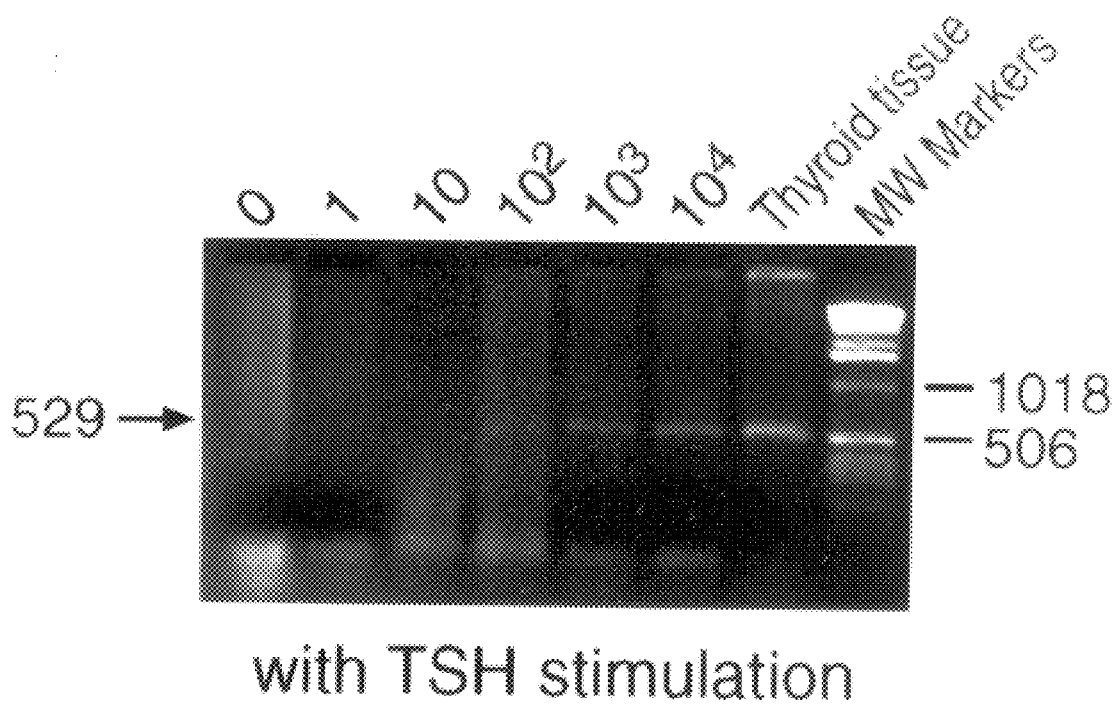

FIGS. 5A and 5B

5A. Sensitivity of reverse transcriptase polymerase chain reaction (RT-PCR) assay determined by analysis of diluted human follicular thyroid cells. RNA was extracted from serial dilutions of human follicular thyroid cells in 5 cc whole blood. A single band of approximately 529 bp was identified when $10^3$ cells per mL were analyzed. No band was identified in unspiked blood.

5B. As above except with thyroid stimulating hormone (TSH) stimulation. A single band of approximately 529 bp was identified when $10^2$ cells per mL were analyzed. No band was identified in unspiked blood.

Figure 6A:
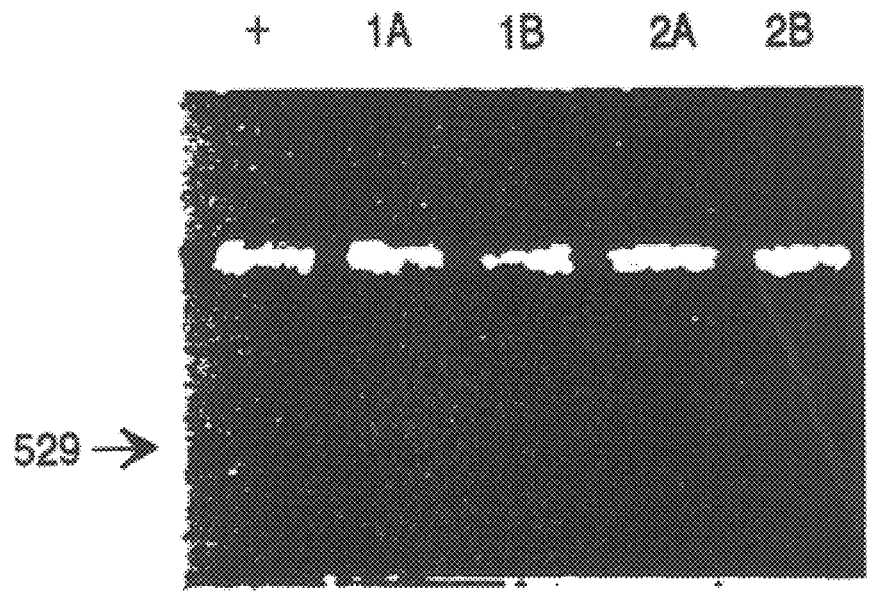
Figure 6B:
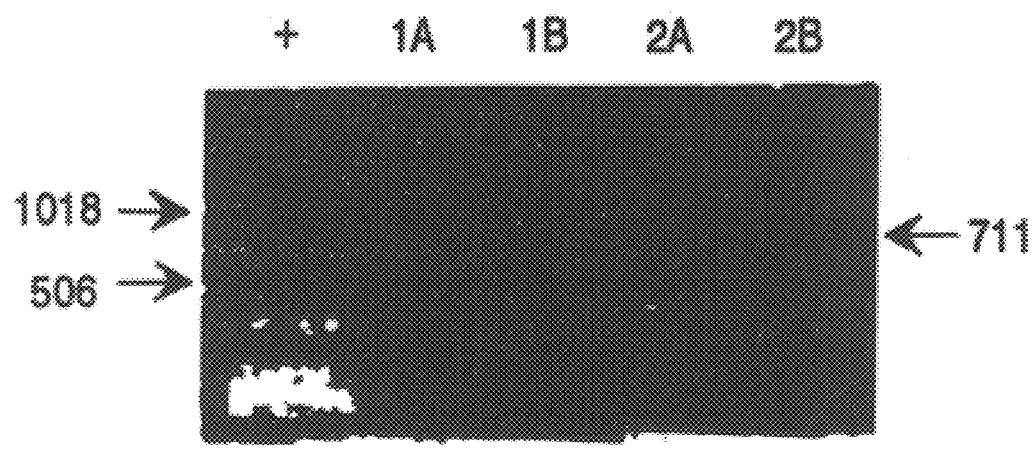

FIGS. 6A and 6B

6A. RT-PCR assay identifies expression of thyroglobulin (approximately 529 bp band) in the peripheral blood of thyroid cancer patients. Samples were obtained from thyroid cancer patients immediately before (B) and after (A) thyroid surgery, and in a specimen of human thyroglobulin (+) in patient #1 this band was identified in both the pre- and postoperative blood samples. However, in patient #2, this band was only identified during the immediate postoperative period. The inability to detect thyroglobulin synthesizing cells in the preoperative peripheral blood samples of patient #2 is demonstrated by the absence of the 529 bp band.

6B. Human glyceraldehyde 3-phosphate dehydrogenase (GAPDH) reverse transcriptase polymerase chain reaction (RT-PCR). GAPDH primers were utilized in a parallel reaction and these primers amplified the appropriate 711 bp fragment from all specimens.

FIGS. 7A, 7B, 7C and 7D

7A. Sequence of primer used to detect thyroid peroxidase. Primer P1 (Seq. ID No. 4).

7B. Sequence of primer used to detect thyroid peroxidase. Primer P2 (Seq. ID No. 5).

7C. Sequence of thyroid peroxidase RT-PCR fragment using primer P1 (Seq. ID No. 6).

7D. Sequence of thyroid peroxidase RT-PCR fragment using primer P2 (Seq. ID No. 7).

DETAILED DESCRIPTION OF THE INVENTION

This invention provides a method of detecting metastatic thyroid cancer in a subject which comprises detecting circulating thyroid cells in a bodily fluid sample of the subject by obtaining an appropriate nucleic acid sample from the bodily fluid sample of the subject; and determining whether the nucleic acid sample contains a marker sequence.

As described herein, "marker sequence" means a sequence that encodes a protein that is specifically expressed in only thyrocytes. Thyroglobulin and thyroid peroxidase are two examples of protein that are expressed in only thyroid cells. One skilled in art could determine other proteins that are expressed soley in thyroid cells using well-known methods and techniques. After such determination, one could determine the sequence of such protein using known methods in the art, e.g. Sanger's dideoxy method.

As describe herein, "bodily fluid sample" includes any fluid sample from the body of the subject that one can obtain a nucleic acid sample so as to determine whether the nucleic acid sample contains the marker sequence. One such example is blood, specifically peripheral blood. However, one skilled in the art could obtain other bodily fluid samples, such as bronchial fluids, that would be able to determine whether the sampel contains a marker sequence so as to determine whether circulating thyrocytes exist.

One skilled in the art could be able to practice the subject invention in various subjects, e.g. animals, but specifically humans.

In a specific embodiment of the above-described method, this invention provides wherein the marker sequence comprises mRNA corresponding to the reverse transcript of DNA encoding thyroglobulin. One detects the marker sequence by amplifying the nucleic acid present in the nucleic acid sample and detecting the presence of thyroglobulin in the resulting amplified nucleic acid.

One can amplify the nucleic acid by using a pair of appropriate primers.

An example of appropriate primers comprise a first primer complementary to exon 1 of the nucleic acid molecule encoding thyroglobulin and a second primer complementary to exon 5 of the nucleic acid molecule encoding thyroglobulin. Specifically, one primer is 5'-GCCTCCATCTGCTGGGTGTC-3' SEQ ID NO: 1 and another primer is 5'-CTCCCTCCGCAGAACACTGGGGT-3' SEQ ID NO: 2.

As used herein, "appropriate primer" means any nucleic acid molecule, naturally or synthetically available, that is able to amplify the nucleic acids that correspond to the marker sequence in the nucleic acid sample so as detect the marker sequence. For example, based on the known technology of polymerase chain reaction, one could design primers appropriate for use in the above-described method using well-known methods in the art, e.g. DNA synthesizer.

In a specific embodiment of the above-described method, this invention provides wherein the marker sequence comprises mRNA corresponding to the reverse transcript of DNA encodes thyroid peroxidase. One can detect the marker sequence by amplifying the nucleic acid present in the nucleic acid and detecting the presence of thyroid peroxidase in the resulting amplified nucleic acid.

One can amplify the above-described method by using two primers. Specifically, one primer is 5'-AGGAGTCTCGTGTCTCTAG-3' SEQ ID NO: 4 and another primer is 5'-GACTGAAGCCGTCCTCATA-3' SEQ ID NO: 5.

This invention further provides a test kit for performing the above-described method.

In a specific embodiment of the test kit, the kit comprises a pair of primers, such that one primer is 5'-GCCTCCATCTGCTGGGTGTC-3' SEQ ID NO: 1 and another primer is 5'-CTCCCTCCGCAGAACACTGGGGT-3' SEQ ID NO: 2.

In another specific embodient, the kit comprises a pair of primers, such that one primer is 5'-GCCTCCATCTGCTGGGTGTC-3' SEQ ID NO: 1 and the other primer is 5'-GACTGAAGCCGTCCTCATA-3' SEQ ID NO: 5.

This invention is illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

FIRST SET OF EXPERIMENTS

METHODS

1. Patients

After approval by the human study committee and protocol review boards, postoperative thyroid cancer patients at Columbia-Presbyterian Medical Center were invited to participate in this project. Postoperative peripheral blood samples from 100 patients, including patients with known metastatic thyroid cancer (6 papillary and 3 follicular cancers) and patients with thyroid cancer and no evidence of current disease (63 papillary, 10 follicular and 5 patients with both papillary and follicular cancers). In addition, six postoperative benign thyroid disease (nontoxic nodular goiters) patients and seven healthy control volunteers were recruited for the study.

The study includes: 77 females and 23 males with an average age of 53 years. Blood samples were collected from each participant during a routine follow-up appointment at various time intervals, from one day to 35 years after thyroid surgery, with an average follow-up of 8.3 years. Patient information, including history, operative reports, pathology reports, physical exam and laboratory and radiographic studies, was obtained by independent chart review. Investigators who performed the RT-PCR assay were blinded to the patients' clinical characteristics, and the clinical investigators were blinded to the RT-PCR results. No clinical decisions were made based on the results of this assay.

Patients were determined to be disease free by a combination of clinical examination, laboratory and radiographic tests. Operations were individualized for each patient, ranging from partial to total thyroidectomies with or without unilateral or bilateral modified or radical neck dissections. All patients with metastatic disease underwent at least total thyroidectomies.

2. Blood Preparation for RNA Extraction

Approximately five mL of venous blood was obtained using standard venipuncture technique, and immediately mixed with 10 mL of RNA STAT 60 (TEL-TEST "B , INC., Friendswood, Tex.) and stored at −20° C. until RNA extraction.

3. RNA Extraction

Total cellular RNA was extracted from a thyroid follicular tumor cell line (UCLA R0 82 W-1, a generous gift from G. J. F. Juillard, Los Angeles, Calif.) (Van Herle, A. J., 1990), thyroid tissue obtained from patients undergoing thyroidectomy, and whole blood samples from patients and normal individuals using RNA STAT-60 according to manufacturer's instructions. The RNA pellet was washed with cold 75% ethanol, dried, dissolved in DEPC treated water and stored at −80° C. RNA concentrations were determined by measuring OD at 260 and 280 nm.

4. Oligonucleotide Primers

Figures 1A, 1B:
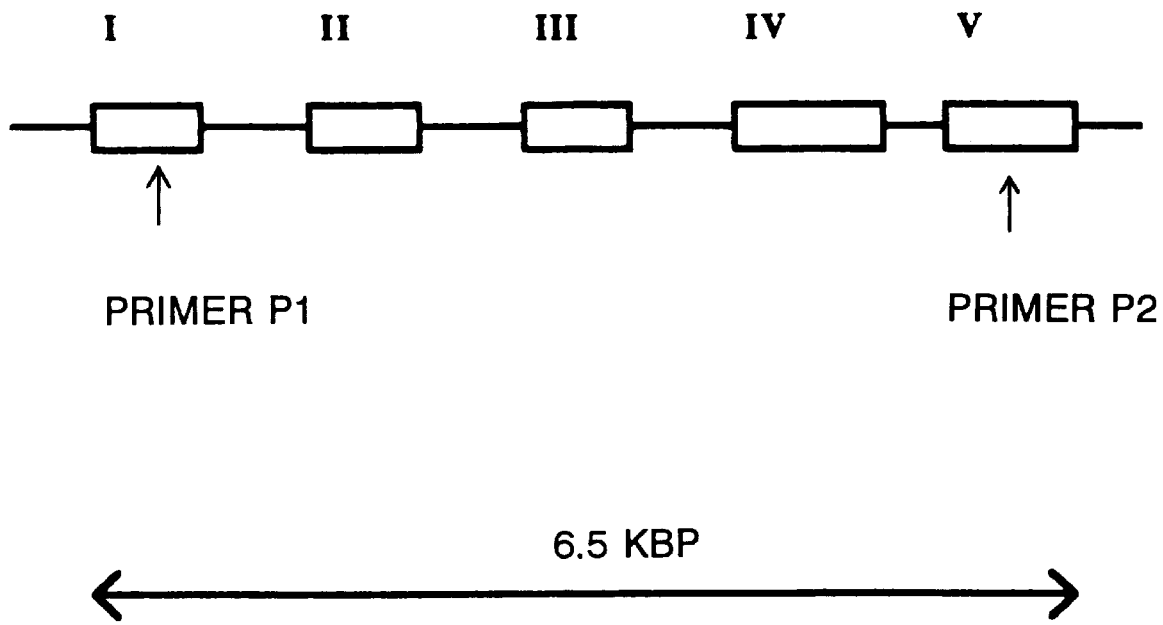
FIGS. 1A and 1B

Two primers (P1 and P2) were custom designed with high specificity to the thyroglobulin gene (FIG. 1A). All primers were synthesized and gel purified by Genset (La Jolla, Calif.). These probes bind exons I and V (FIG. 1B). Primers span a genomic DNA length of approximately 6.5 kb and bind sequences such that RT-PCR amplification yield an appromixately 529 base-pair transcript (FIG. 2A).

5. Reverse Transcriptase-Polymerase Chain Reaction (RT-PCR)

RT-PCR was carried out as described by Burchill (Burchill, S. A., et al., 1994). In brief, 1 ug of total RNA was reverse transcribed with 200 units of Superscript™ II (Gibco-BRL, Maryland) in 20 uL of RT stock buffer containing PCR buffer (200 mM Tris.HCl, pH 8.4, 500 mM KCl), 5 mM $MgCl_2$, 500 uM dNTP, 10 U RNase inhibitor (Gibco-BRL), and 100 pmoles of primer P2. The reaction mixture was covered with 20 uL of mineral oil and the reverse transcription was allowed to proceed at 38° C. for 2 h . Then 80 uL of PCR master mixture containing PCR buffer (200 mM Tris.HCl, pH 8.4, 500 mM KCl), 1.25 mM $MgCl_2$, 100 pmoles primer P1 and P2, and 2.5 units of Taq DNA polymerase (Gibco-BRL, Maryland) was added. PCR was carried out in a thermocycler (Barnsted/Thermolyne, Iowa) with an initial denaturation at 94° C. for 5 min., followed by 35 cycles of 94° C. for 1 min., 58° C. for 2 min., 72° C. for 3 min. Additional extension at 72° C. for 15 min. was allowed to proceed and then the sample was cooled to 4° C. Twenty uL of the RT-PCR product was separated in a 2% agarose gel containing ethidium bromide (0.5 ug/mL) and visualized on a transilluminator. One kb DNA ladder molecular weight marker (Gibco BRL, Maryland) was used as a standard.

To confirm the integrity of RNA, RT-PCR was performed with human glyceraldehyde 3-phosphate dehydrogenase (GAPDH) primers 5'-CGTCTTCACCACCATGGAGAA-3' SEQ ID NO: 8 and 5'-CATGGCCTCCAAGGAGTAAGA-3' SEQ ID. NO: 9 (GenBank accession number J02642) as described before (Jiang, H., et al., 1994) (FIG. 2B).

6. Restriction Enzyme Digestion of RT-PCR Amplified Thyroglobulin Fragment

All RT-PCR amplified thyroglobulin fragments were isolated from agarose gels by electroelution, ethanol precipitated and DNA pellets were dissolved in TE (pH 8.0) buffer (Sambrook, J., et al., 1989). Approximately 1 ug DNA sample was digested with restriction enzyme Bgl II (Gibco-BRL) at 37° C. for 2 h. and analyzed on 2% agarose gel containing ethidium bromide (0.5 ug/mL) as above (FIG. 3).

7. Cloning and Sequencing of RT-PCT Amplified Thyroglobulin Fragment

RT-PCR amplified thyroglobulin fragment from human thyroid tissue RNA was cloned into TA cloning vector pCR II (Invitrogen, California) according to manufacturer's instructions and sequenced by Sanger's dideoxynucleotide chain termination method (Sanger, F., et al., 1989)) using SP6 and T7 primers.

8. Thyroglobulin RT-PCR Sensitivity Assay

Thyroglobulin RT-PCR sensitivity was determined by spiking thyroid follicular carcinoma cells (UCLA R0 82 W-1) (Van Herle, A. J., et al., 1990) into whole blood samples from normal donors. Ten fold serial dilutions of thyroid follicular carcinoma cells were mixed with 5 mL aliquots of whole blood and RNA was isolated as described before. RT-PCR was performed using 1 ug of total RNA and analyzed as described above (FIG. 5A). In a second experiment thyroid follicular carcinoma cells were stimulated in culture with thyroid stimulating hormone (TSH from bovine pituitary, Sigma Chem. Co., Missouri) at a concentration of 5 uU/mL for 5 days, and the stimulated cells were spiked as above, RNA was isolated and RT-PCR was performed as before (FIG. 5B).

RESULTS

1. Detection of Thyroglobulin Transcripts by RT-PCR

FIGS. 1A and B show thyroglobulin transcript primers P1 (sense) and P2 (antisense), and their relative positions in the thyroglobulin gene. Thyroglobulin transcripts were detected as an approximately 529 bp amplification fragment in human thyroid follicular cell line, human thyroid tissue and whole blood of metastatic thyroid cancer patients by reverse transcription of RNA using primer P2 followed by PCR with primers P1 and P2. FIG. 2A shows examples of thyroglobulin fragment amplification in thyroid tissue of a patient, and peripheral blood of another patient with metastatic thyroid cancer. Such an amplification band was not visible in the peripheral blood of patients with benign thyroid disease and healthy controls. Intactness of RNA in all cases was confirmed by running an RT-PCR in parallel with human glyceraldehyde 3-phosphate dehydrogenase (GAPDH) primers. In each case an amplification band of 711 bp was evident in the gel (FIG. 2B).

2. Restriction Enzyme Fragmentation and Nucleotide Sequence Verification of RT-PCR Amplified Fragments All thyroglobulin RT-PCR fragments were further analyzed by Bgl II restriction enzyme digestion. FIG. 3 shows a few such analyses. As expected in each case two restriction fragments of 272 and 257 bp were revealed confirming the restriction site in the amplified thyroglobulin fragment. Undigested controls were included in each case in the gel analysis.

In two representative cases the RT-PCR amplified thyroglobulin fragments were cloned into pCR II vector (Invitrogen, California) and sequenced in both directions using SP6 and T7 primers by dideoxynucleotide chain termination method of Sanger et al (Sanger, F., et al., 1977). The derived nucleotide sequences of RT-PCR amplified thyroglobulin fragments were identical to the nucleotide sequence of thyroglobulin reported in the Gen Bank (Accession number 02154) (Jiang, H., et al., 1994) (FIG. 4). This further confirmed that the amplified fragments were derived from thyroglobulin transcripts.

3. Determination of Sensitivity of Thyroglobulin RT-PCR Assay

To determine the sensitivity of this assay initially unstimulated human thyroid follicular tumor cells (UCLA RO82 W-1) were used for spiking into peripheral blood of a normal donor. FIG. 5A shows a faint band at 529 bp when the serial dilution reached to $10^3$ tumor cells in 5 mL blood suggesting the detection limit of 200 tumor cells/mL blood. However, when the cell spiking experiment was repeated with bovine pituitary thyroid stimulating hormone (TSH) stimulated thyroid follicular tumor cells, 529 bp RT-PCR band was visible in serial dilution up to $10^2$ tumor cells in 5 mL blood (FIG. 5B). Thus there was a 10 fold increase in sensitivity with a detection limit of 20 tumor cells/mL blood. All specimens of human thyroid tissue were found to be positive for thyroglobulin mRNA.

4. Patients

Postoperative peripheral blood samples were obtained from 100 patients, including patients with known metastatic thyroid cancer (6 papillary and 3 follicular cancers), thyroid cancer and no evidence of current metastases (63 papillary, 10 follicular and 5 patients with both papillary and follicular cancers), benign thyroid disease (6 nontoxic nodular goiters) and normal volunteers (Seiden, M. V., et al., 1994). Thyroglobulin transcripts were detected in 9/9 patients with metastatic thyroid cancer, 7/78 patients without current metastases, 0/6 patients with benign thyroid disease and 0/7 normal volunteers (Table 1).

TABLE 1

Comparison of PCR to clinical staging in postoperative patients

|  |  | RT-PCR |
| --- | --- | --- |
| Papillary thyroid |  | 12/69 |
|  | With current metastates | 6/6 |
|  | Without current metastates | 6/63 |
|  | Metastates previously | 5/22 |
|  | No history of | 1/41 |
| Follicular thyroid |  | 3/13 |
|  | With current metastases | 3/3 |
|  | Without current metastases | 0/10 |
| Papillary and |  | 1/5 |
|  | With current metastases | 1/5 |
|  | Without current metastases | 0/0 |
| Benign thyroid |  | 0/6 |
| Control volunteers |  | 0/7 |

The patients without current metastases (n=78) were further subdivided into patients who had a history of metastatic disease that had been successfully treated with either radioactive iodine or surgery (n=22) and those who never had any metastatic disease (n=56). Of the patients who had been successfully cured of metastatic thyroid cancer, 5 were positive by PCR analysis. These five patients represent patients who had papillary thyroid cancer that was metastatic to lymph nodes.

Two additional patients had thyroglobulin transcripts detected in peripheral blood samples. One patient with a papillary thyroid cancer had a concurrent parathyroid cancer, and one patient had both papillary and follicular thyroid cancers. In addition, there were four other patients with both papillary and follicular thyroid cancers who tested negative by RT-PCR analysis.

Not all patients underwent serum thyroglobulin tests. However, the range of serum thyroglobulin levels for patients with documented metastatic disease ranged from 16 to 46,000 and did not always correlate with extent of disease. Not all patients were taken off their thyroid hormone prior to obtaining serum thyroglobulin levels. Four of the seven RT-PCR positive thyroid cancer patients without current metastatic disease had serum thyroglobulin levels drawn; all of these tests were normal. In addition, three of these seven patients underwent total body $^{131}$I scans which were also negative for metastatic disease.

CONCLUSIONS

Until recently, small numbers of circulating tumor cells could not be detected in the peripheral blood (Goldblatt, S. A., and Nadel, E. M., 1965). However, with the advent of PCR, it is now possible to amplify tumor-specific transcripts by RT-PCR. These techniques have been used to identify blood-borne tumor cells in several solid cancers including melanoma, prostate and neuroblastoma (Moreno, J. G., et al., 1992; Katz, A. E., et al., 1994; Seiden, M. V., et al., 1994; Mattano, L. A., et al., 1992; Burchill, S. A., et al., 1994; Johnson, P. W. M., et al., 1995). In prostate cancer especially, the detection of prostate-specific antigen sequences has been shown to correlate with the extent of disease (Katz, A. E., et al., 1994).

Using RT-PCR technique, a test for the detection of blood-borne thyroglobulin synthesizing cells was developed. Because thyroglobulin is secreted only by thyroid cells, we believe these circulating cells are thyrocytes. Currently, the limit of sensitivity of this assay using TSH stimulated follicular thyroid cells is 20 cells/mL of whole blood. Burchill et al cite a sensitivity of 1–10 cells per mL of whole blood when utilizing RT-PCR for the detection of neuroblastoma cells (Burchill, S. A., et al., 1994). Thyrocytes were identified in all patients with metastatic thyroid cancer, but not in any of the control patients with benign thyroid disease.

Of the 78 thyroid cancer patients tested who appeared to be clinically disease free (by physical exam, serum thyroglobulin level and/or $^{131}$I total body scanning), 7 patients were positive by RT-PCR assay. These patients include 5 patients with papillary thyroid cancer who had been treated for lymph node metastases in the past, as well as one patient with papillary thyroid cancer and a concurrent parathyroid cancer and one patient with both papillary and follicular thyroid cancers. This subset of RT-PCR positive patients could represent false positives, or they may signify subclinical disease. On the other hand, the presence of circulating thyroid cells may be a harbinger of future clinically apparent metastatic disease. Since thyroid cancer is usually a slow growing indolent tumor and disease recurrence is possible decades after the initial treatment, these positive patients may be at risk for the future development of thyroid cancer metastases.

It is generally recognized that papillary thyroid cancers metastasize to the lymph nodes, and follicular cancers are hematogenously disseminated (Braverman, L. E., et al., 1991). Thus it is an unexpected result to find that all six patients with metastatic papillary thyroid cancer were found to have thyrocytes circulating in the peripheral bloodstream. In addition, of the 7 thyroid cancer patients without evidence of disease but with positive RT-PCR results, all had papillary thyroid cancer. This finding further supports the hypothesis that papillary cancers may also metastasize hematogenously. The discovery of circulating thyrocytes in the peripheral blood of patients with metastatic thyroid cancer may be a key to understanding the method of tumor dissemination and spread.

SECOND SET OF EXPERIMENTS

METHODS

1. Patients

All patients undergoing thyroid and/or parathyroid operation at Columbia-Presbyterian Medical Center were invited to participate in this project. Immediate preoperative and postoperative peripheral blood samples were obtained from 36 patents undergoing thyroid or parathyroid operation. These patients included 9 with differentiated thyroid cancer, 19 with benign thyroid disease, 3 with parathyroid adenomas, 4 with differentiated thyroid cancer and parathyroid adenomas and one with both benign thyroid disease and parathyroid adenoma. In addition, 10 of the 36 patients had blood samples drawn 3 weeks postoperatively.

The experiment includes 31 females and 5 males with an average of 50.3 years. Patient information, including history, operative reports, pathology reports, physical exam and laboratory and radiographic studies, was obtained by independent chart review. Investigators who performed the RT-PCR assay were blinded to the patients' clinical characteristics, and the clinical investigators were blinded to the RT-PCR results. No clinical decisions were made based on the results of this assay.

Operations were individualized for each patient, ranging from partial to total thyroidectomies with or without neck exploration and parathyroidectomy, depending on the clinical indications. All patients with thyroid cancer underwent total thyroidectomy.

2. Blood Preparation for RNA Extraction

Approximately five mL of venous blood was obtained using standard venipuncture technique, and immediately mixed with 10 mL of RNA STAT 60 (TEL-TEST "B , INC., Friendswood, Tex.) and stored at −20° C. until RNA extraction.

3. RNA Extraction

Total cellular RNA was extracted from a thyroid follicular tumor cell line (UCLA R0 82 W-1, a generous gift from G. J. F. Juillard, Los Angeles, Calif.) (Van Herle, A. J., 1990), thyroid tissue obtained from patients undergoing thyroidectomy, and whole blood samples from patients and normal individuals using RNA STAT-60 according to manufacturer's instructions. The RNA pellet was washed with cold 75% ethanol, dried, dissolved in DEPC treated water and stored at −80° C. RNA concentrations were determined by measuring OD at 260 and 280 nm.

4. Oligonucleotide Primers

Two primers (P1 AND P2) were custom designed with high specificity to the thyroglobulin gene (FIG. 1A). All primers were synthesized and gel purified by Genset (La Jolla, Calif.). These primers bind exons I and V (FIG. 1B). Primers span a genomic DNA length of approximately 6.5 kb and bind sequences such that RT-PCR amplification yield an appromixately 529 base-pair transcript.

5. Reverse Transcriptase-polymerase Chain Reaction (RT-PCR)

RT-PCR was carried out as described by Burchill (Burchill, S. A., et al., 1994). In brief, 1 ug of total RNA was reverse transcribed with 200 units of Superscript™ II (Gibco-BRL, Maryland) in 20 uL of RT stock buffer containing PCR buffer (200 mM Tris.HCl, pH 8.4, 500 mM KCl), 5 mM MgCl$_2$, 500 uM dNTP, 10 U RNase inhibitor (Gibco-BRL), and 100 pmoles of primer P2. The reaction mixture was covered with 20 uL of mineral oil and the reverse transcription was allowed to proceed at 38° C. for 2 h . Then 80 uL of PCR master mixture containing PCR buffer (200 mM Tris.HCl, pH 8.4, 500 mM KCl), 1.25 mM MgCl$_2$, 100 pmoles primer P1 and P2, and 2.5 units of Taq DNA polymerase (Gibco-BRL, Maryland) was added. PCR was carried out in a thermocycler (Barnsted/Thermolyne, Iowa) with an initial denaturation at 94° C. for 5 min., followed by 35 cycles of 94° C. for 1 min., 58° C. for 2 min., 72° C. for 3 min. Additional extension at 72° C. for 15 min. was allowed to proceed and then the sample was cooled to 4° C. Twenty uL of the RT-PCR product was separated in a 1.6% agarose gel containing ethidium bromide (0.5 ug/mL) and visualized on a transilluminator. One kb DNA ladder molecular weight marker (Gibco BRL, Maryland) was used as a standard.

To confirm the integrity of RNA, RT-PCR was performed with human glyceraldehyde 3-phosphate dehydrogenase (GAPDH) primers 5'-CGTCTTCACCACCATGGAGAA-3' SEQ ID NO: 8 and 5'-CATGGCCTCCAAGGAGTAAGA-3' SEQ ID NO: 9 (GenBank accession number J02642) as described previously (Jiang, H., et al., 1994).

6. Restriction Enzyme Digestion of RT-PCR Amplified Thyroglobulin Fragment

All RT-PCR amplified thyroglobulin fragments were isolated from agarose gels by electroelution, ethanol precipitated and DNA pellets were dissolved in TE (pH 8.0) buffer (Sambrook, J., et al., 1989). Approximately 1 ug DNA sample was digested with restriction enzyme Bgl II (Gibco-BRL) at 37° C. for 2 h. and analyzed on 1.6% agarose gel containing ethidium bromide (0.5 ug/mL) as above.

7. Cloning and Sequencing of RT-PCT Amplified Thyroglobulin Fragment

RT-PCR amplified thyroglobulin fragment from human thyroid tissue RNA was cloned into TA cloning vector pCR II (Invitrogen, California) according to manufacturer's instructions and sequenced by Sanger's dideoxynucleotide chain termination method (Sanger, F., et al., 1989) using SP6 and T7 primers.

8. Thyroglobulin RT-PCR Sensitivity Assay

Thyroglobulin RT-PCR sensitivity was determined by adding thyroid follicular carcinoma cells (UCLA R0 82 W-1) (Van Herle, A. J., et al., 1990) into whole blood samples from normal donors. Ten fold serial dilutions of thyroid follicular carcinoma cells were mixed with 5 mL aliquots of whole blood and RNA was isolated as described before. RT-PCR was performed using 1 ug of total RNA and analyzed as described above. In a second experiment, thyroid follicular carcinoma cells were stimulated in culture with thyroid stimulating hormone (TSH from bovine pituitary, Sigma Chem. Co., Missouri) at a concentration of 5 uU/mL for 5 days, and the stimulated cells were added as above. RNA was isolated and RT-PCR was performed as before.

RESULTS

1. Detection of Thyroglobulin Transcripts by RT-PCR

FIGS. 1A and 1B show thyroglobulin transcript primers P1 (sense) and P2 (antisense), and their relative positions in the thyroglobulin gene. Thyroglobulin transcripts were detected as a 529 bp amplicon in the human thyroid follicular cell line, human thyroid tissue and whole blood from metastatic thyroid cancer patients by reverse transcription of RNA primers P1 and P2.

FIG. 6A shows an example of thyroglobulin fragment amplification in peripheral blood of a patient with benign thyroid disease immediately after thyroid operation, but no such amplification was evident preoperatively. Integrity of RNA in all cases was confirmed by running an RT-PCR in parallel with human glyceraldehyde 3-phosphate dehydrogenase (GAPDH) primers. In each case, an amplification of 711 bp was evident in the gel (see FIG. 6B).

2. Restriction Enzyme Fragmentation and Nucleotide Sequence Verification of RT-PCR Amplified Fragments All thyroglobulin RT-PCR fragments were further analyzed by Bgl II restriction enzyme digestion. FIG. 3 shows a few such analyses. As expected in each case two restriction fragments of 272 and 257 bp were revealed confirming the restriction site in the amplified thyroglobulin fragment. Undigested controls were included in each case in the gel analysis.

In two representative cases the RT-PCR amplified thyroglobulin fragments were cloned into pCR II vector (Invitrogen, California) and sequenced in both directions using SP6 and T7 primers by dideoxynucleotide chain termination method of Sanger et al (Sanger, F., et al., 1977). The derived nucleotide sequences of RT-PCR amplified thyroglobulin fragments were identical to the nucleotide sequence of thyroglobulin reported in the Gen Bank (Accession number 02154) (Jiang, H., et al., 1994) (FIG. 4). This further confirmed that the amplified fragments were derived from thyroglobulin transcripts.

3. Patients

Postoperative peripheral blood samples were obtained from 36 patients undergoing thyroid or parathyroid operation. These patients included 9 with differentiated thyroid cancer, 19 with benign thyroid disease, 3 with parathyroid adenomas, 4 with differentiated thyroid cancer and parathyroid adenomas and one with both benign thyroid disease and parathyroid adenoma. Preoperatively, thyroglobulin transcripts were detected in 10 or 36, including 2 patients with differentiated thyroid cancer, 6 with benign thyroid cancer and 2 with parathyroid adenoma. Fourteen of 36 patients were RT-PCR positive immediately following the operation (5 patients with differentiated thyroid cancer, 6 with benign thyroid cancer, 2 with parathyroid adenoma, and 1 with differentiated thyroid cancer and parathyroid adenoma. Additionally, 10 of the 36 patients had blood samples drawn three postoperatively. Only 1 of these 10 RT-PCR assays was positive in a patient with papillary thyroid cancer. These data are displayed in Table 2.

TABLE 2

Comparison of PCR to Clinical Staging in Immediate Preoperative, Immediate Postoperative and 3 Week Postoperative Patients

| Patient # | Diagnosis | Preoperative | Postoperative | Postoperative (3 wks) |
|---|---|---|---|---|
| 1 | C | + | + | NA |
| 2 | C | − | + | NA |
| 3 | PA | − | − | NA |
| 4 | B | − | − | NA |
| 5 | B | − | − | NA |
| 6 | B | − | − | NA |
| 7 | B | + | + | NA |
| 8 | PA | + | + | NA |
| 9 | C + PA | − | − | − |
| 10 | C | − | + | + |
| 11 | B | − | − | − |
| 12 | PA | + | + | − |
| 13 | C | − | − | − |
| 14 | C | − | + | − |
| 15 | C + PA | − | − | − |

TABLE 2-continued

Comparison of PCR to Clinical Staging in Immediate Preoperative, Immediate Postoperative and 3 Week Postoperative Patients

| Patient # | Diagnosis | Preoperative | Postoperative | Postoperative (3 wks) |
|---|---|---|---|---|
| 16 | B + PA | − | − | NA |
| 17 | C | − | − | − |
| 18 | B | − | − | − |
| 19 | B | − | − | NA |
| 20 | C | + | − | NA |
| 21 | B | + | + | − |
| 22 | B | + | + | NA |
| 23 | C | − | − | NA |
| 24 | C + PA | − | + | NA |
| 25 | C + PA | − | − | NA |
| 26 | B | + | − | NA |
| 27 | B | − | − | NA |
| 28 | C | − | + | NA |
| 29 | B | − | + | NA |
| 30 | B | − | + | NA |
| 31 | B | − | − | NA |
| 32 | B | + | − | NA |
| 33 | B | − | + | NA |
| 34 | B | + | − | NA |
| 35 | B | − | − | NA |
| 36 | B | − | − | NA |

B; benign thyroid disease;
C: differentiated thyroid cancer,
PA: parathyroid adenoma,
B + PA: benign thyroid disease and parathyroid adenoma,
C + PA: differentiated thyroid cancer and parathyroid adenoma.

CONCLUSIONS

It is generally recognized that papillary thyroid cancers metastasize to the lymph nodes, and follicular cancers are hematogenously disseminated. The findings further support the hypothesis that papillary cancers may also metastsize hematogenously.

The initial discovery of circulating thyrocytes in the peripheral blood of postoperative patients with metastatic thyroid cancer led to investigations into the biological significance of these finds. Specifically, in patients with intact but diseased thyroids, both benign and malignant, would these patients shed thyrocytes into the peripheral circulation? It was hypothesized that both benign and malignant thyroid disorders might cause these cells to be shed into the bloodstream. The immediate postoperative period in thyroid cells is a special situation; manipulation and incising thyroid tissue may allow thyrocytes to enter the bloodstream and circulate briefly. Therefore, circulating thyroid cells should be detected in a larger number of patients. However, if there is no residual disease, the "false" positives should clear several weeks after surgery. Only those patients with malignant disease capable of metastasizing through the blood stream should have detectable thyrocytes which persist after the immediate postoperative period.

Circulating thyrocytes in 28% of the patients who were about to undergo thyroid or parathyroid surgery were identified. Immediately, postoperatively, however that number increased to 39%; this increase is believed due to spillage of thyroid cells during thyroid operation or neck exploration for hyperparathyroidism. Finally, by three weeks postoperative, only one of ten patients had residual circulating thyroid cells. This patient had undergone total thyroidectomy for papillary thyroid cancer. Thus, it is believed this patient represents a true positive.

The RT-PCR assay for thyroglobulin transcripts that has been developed appears to have preoperative limitations. The presence of thyroid disease, either malignant or benign, may cause a positive assay in the preoperative period. Additionally, operative thyroid manipulation appears to cause an increase number of false positives immediately after the operation. By several week postoperatively, however, the majority of patients clear these circulating thyrocytes, and evidence of disease. These data support use of the RT-PCR assay for circulating cells with thyroglobulin transcripts as long term postoperative tests to identify early metastatic thyroid disease.

THIRD SET OF EXPERIMENTS

Since thyroid peroxidase is actively expressed only in thyrocytes, similarly to thyroglobulin, one could utilize the methods described in the two previously described set of experiments and use RT-PCR to detect mRNA transcripts of thyroid peroxidase.

Based on the known cDNA sequence of thyroid peroxidase, primers were custom-designed as described in the earlier experiments. The sequences of these primers are given in FIGS. 7A and 7B. After amplification, the RT-PCR fragments were sequenced (FIGS. 7C and 7D).

In combination with the information available, one skilled in the art could detect thyroid cancer by detecting circulating thyrocytes that actively express thyroid peroxidase using RT-PCR.

REFERENCES

1. Braverman, L. E., et al. (1991) *The thyroid a fundamental and clinical text.* 6th ed. Philadelphia: JB Lippincott Company, p. 1142.
2. Burchill, S. A., et al. (1994) "Neuroblastoma cell detection by reverse transcriptase-polymerase chain reaction (RT-PCR) for tyrosine hydroxylase mRNA." *Int. J. Cancer* 57: 671–675.
3. Cady, B. and Rossi, R. L. (1991) *Surgery of the thyroid and parathyroid glands.* 3rd ed. Philadelphia: WB Saunders Company, p. 139.
4. Goldblatt, S. A. and Nadel, E. M. (1965) "Cancer cells in the circulating blood: a critical review II." *Acta Cytologica* 9: 6–20.
5. Jiang, H., et al. (1994) "Induction of differentiation in human promyelocytic HL-60 leukemia cells activates p21, WAF1/CIP1, expression in the abscence of p53." *Oncogene* 9: 3397–3406.
6. Johnson, P. W. M., et al. (1995) "The molecular detection of circulating tumour cells." *British Journal of Cancer* 72: 268–276.
7. Katz, A. E., et al. (1994) "Molecular staging of prostate cancer with the use of an enhanced reverse transcriptase-PCR assay." *Urology* 43: 765–775.
8. Lo Gerfo, P., et al. (1979) "Thyroglobulin in benign and malignant thyroid disease." *JAMA* 241: 923–925.
9. Mattano, L. A., et al. (1992) "Sensitive detection of rare circulating neuroblastoma cells by the reverse transcriptase-polymerase chain reaction." *Cancer Research* 52: 4701–4705.
10. Moreno, J. G., et al. (1992) "Detection of hematogenous micrometastasis in patients with prostate cancer." *Cancer Research* 52: 6110–6112.
11. Sambrook, J., et al. (1989) *Molecular cloning: a laboratory manual.* 2nd ed. New York: Cold Spring Harbor Laboratory Press.

12. Sanger, F., et al. (1977) "DNA sequencing with chain-terminating inhibitors." Proc. Natl. Acad. Sci. 74: 5463.

13. Seiden, M. V., et al. (1994) "Detection of circulating tumor cells in men with localized prostate cancer." Journal of Clinical Oncology 12: 2634–2639.

14. Shah, J. P. and Lydiatt, W. (1995) "Treatment of cancer of the head and neck." CA Cancer J Clin 45: 352–368.

15. Van Herle, A. J., et al. (1990) "Effects of 13 cis-Retinoic acid on growth and differentiation of human follicular carcinoma cells (UCLA R0 82 W-1) in Vitro." Journal of Clinical Endocrinology and Metabolism 71: 755–763.

What is claimed is:

1. A method of detecting metastatic thyroid cancer in a subject which comprises detecting circulating thyroid cells in a bodily fluid sample of the subject by:
   (a) obtaining a nucleic acid sample from the bodily fluid sample of the subject; and
   (b) determining whether the nucleic acid sample from step (a) contains a marker sequence specific for thyroid cells so as to thereby detect metastatic thyroid cancer in the subject.

2. The method of claim 1, wherein the marker sequence comprises mRNA encoding thyroglobulin, and wherein the determining of step (b) comprises:
   (i) amplifying a reverse transcript of the thyroglobulin encoding mRNA present in the nucleic acid sample of step (a); and
   (ii) detecting the presence of the reverse transcript of the thyroglobulin encoding mRNA in the resulting amplified nucleic acid.

3. The method of claim 2, wherein the amplification of step (I) is performed with a pair of primers that are complementary to the reverse transcript.

4. The method of claim 3, wherein the primers that are complementary to the reverse transcript comprise a first primer complementary to exon 1 of the nucleic acid encoding thyroglobulin and a second primer complementary to exon 5 of the nucleic acid encoding thyroglobulin.

5. The method of claim 4, wherein the first primer is 5'-GCCTCCATCTGCTGGGTGTC-3' SEQ ID NO: 1.

6. The method of claim 4, wherein the second primer is 5'-CTCCCTCCGCAGAACACTGGGGT-3' SEQ ID NO: 2.

7. The method of claim 1, wherein the marker sequence comprises mRNA encoding thyroid peroxidase, and wherein the determining of step (b) comprises:
   (i) amplifying a reverse transcript of thyroid Peroxidase encoding mRNA present in the nucleic acid sample of step (a); and
   (ii) detecting the presence of the reverse transcript of the thyroid peroxidase encoding mRNA in the resulting amplified nucleic acid.

8. The method of claim 7, wherein the amplification of step (I) is performed with a pair of primers.

9. The method of claim 8, wherein one primer of the pair of primers is 5'-AGGAGTCTCGTGTCTCTAG-3' SEQ ID NO: 4.

10. The method of claim 8, wherein one primer of the pair of primer is 5'-GACTGAAGCCGTCCTCATA-3' SEQ ID NO: 5.

11. The method of claim 1, wherein the bodily fluid sample comprises blood.

12. The method of claim 1, wherein the subject is human.

13. The method of claim 1, wherein the nucleic acid sample is obtained at least three weeks after removal of the thyroid cancer from the subject.

14. A test kit for detecting circulating metastatic thyroid cancer in a subject which comprises a means for detecting a marker sequence, wherein the marker sequence is specific for said thyroid cells and said means for detection is selected from the group consisting of:
   a) a pair of primers, wherein one primer is 5'-GCCTCCATCTGCTGGGTGTC-3' (SEQ ID NO: 1) and another primer is 5'-CTCCCTCCGCAGAACACTGGGGT-3' (SEQ ID NO: 2) and;
   b) a pair of primers, wherein one primer is 5'-AGGAGTCTCGTGTCTCTA G-3' (SEQ ID NO: 4) and another primer is 5'-GACTGAAGCCGTCCTCATA-3' (SEQ ID NO: 5)
   wherein detection of the marker sequence thereby indicating metastatic thyroid cancer in the subject.

* * * * *

SEQUENCE LISTING

<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: OTHER
      NUCLEIC ACID

<400> SEQUENCE: 1
gcctccatct gctgggtgtc                                               20

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: OTHER
      NUCLEIC ACID

<400> SEQUENCE: 2
ctccctccgc agaacactgg ggt                                           23

<210> SEQ ID NO 3
<211> LENGTH: 531
<212> TYPE: DNA
<213> ORGANISM: Artificial Sequence
<220> FEATURE:
<223> OTHER INFORMATION: Description of Artificial Sequence: OTHER
      NUCLEIC ACID

<400> SEQUENCE: 3
ggcctccatc tgctgggtgt cggccaatat cttcgagtac caggttgatg cccagcccct     60
tcgtccctgt gagctgcaga gggaaacggc ctttctgaag caagcagact acgtgcccca    120
gtgtgcagag gatggcagct tccagactgt ccagtgccag aacgacggcc gctcctgctg    180
gtgtgtgggt gccaacggca gtgaagtgct gggcagcagg cagccaggac ggcctgtggc    240
ttgtctgtca ttttgtcagc tacagaaaca gcagatctta ctgagtggct acattaacag    300
cacagacacc tcctacctcc ctcagtgtca ggattcaggg gactacgcgc ctgttcagtg    360
tgatgtgcag catgtcccag tgctggtgtg tggacgcaga ggggatggag gtgtatggga    420
cccgccagct ggggaggcca aagcgatgtc caaggagctg tgaaataaga aatcgtcgtc    480
ttctccacgg ggtgggagat aagtcaccac cccagtgttc tgcggaggga g              531

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:  OTHER
      NUCLEIC ACID

<400> SEQUENCE: 4

```
aggagtctcg tgtctctag                                                19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: OTHER
      NUCLIEC ACID

<400> SEQUENCE: 5
gactgaagcc gtcctcata                                                19

<210> SEQ ID NO 6
<211> LENGTH: 169
<212> TYPE: DNA
<213> ORGANISM: Artificial Sequence
<220> FEATURE:
<223> OTHER INFORMATION: Description of Artificial Sequence: OTHER
      NUCLEIC ACID

<400> SEQUENCE: 6
gtcttggagg aaagcaagcg cctggtggac accgccatgt acgccacgat gcagagaaac    60
ctcaagaaaa gaggaatcct ttctccagct cagcttctgt cttttttccaa acttcctgag   120 ccaacaagcg gagtgattgc ccgagcagca gagataatgg aaacatcaa               169

<210> SEQ ID NO 7
<211> LENGTH: 262
<212> TYPE: DNA
<213> ORGANISM: Artificial Sequence
<220> FEATURE:
<223> OTHER INFORMATION: Description of Artificial Sequence: OTHER
      NUCLEIC ACID

<400> SEQUENCE: 7
gactggaggg agccatcgtg ccagggccgt gttggaggcg ccccatctgg ggtggtctct    60
gttgttgcaa gctcctgtga tgggctgtat tgttcgcca gttgcaatga tgctcagcag   120
atcttctgat aaagcatccg ttggatgctg tgattgttga gttttcaggt tgacttttct   180
tttcatcgct tgtattgatg tttccattat ctctgctgct cggggaatca ctccgcttgt   240
tggctcagga agtttggaaa aa                                           262

<210> SEQ ID NO 8
<211> LENGTH: 21
<212> TYPE: DNA
<213> ORGANISM: HUMAN

<400> SEQUENCE: 8
cgtcttcacc accatggaga a                                             21

<210> SEQ ID NO 9
<211> LENGTH: 21
<212> TYPE: DNA
<213> ORGANISM: HUMAN

<400> SEQUENCE: 9
catggcctcc aaggagtaag a                                             21
```